US005487390A

United States Patent [19]
Cohen et al.

[11] Patent Number: 5,487,390
[45] Date of Patent: Jan. 30, 1996

[54] GAS-FILLED POLYMERIC MICROBUBBLES FOR ULTRASOUND IMAGING

[75] Inventors: Smadar Cohen, Petach-Tickva, Israel; Alexander K. Andrianov, Belmont, Mass.; Margaret Wheatley, Media; Harry R. Allcock, State College, both of Pa.; Robert S. Langer, Newton, Mass.

[73] Assignees: Massachusetts Institute of Technology, Cambridge, Mass.; The Penn State Research Foundation, University Park, Pa.

[21] Appl. No.: 182,216

[22] Filed: Jan. 14, 1994

Related U.S. Application Data

[60] Continuation-in-part of Ser. No. 880,248, May 8, 1992, Pat. No. 5,308,701, which is a division of Ser. No. 593,684, Oct. 5, 1990, Pat. No. 5,149,543.

[51] Int. Cl.$^6$ ............................. A61B 8/14; A61K 9/50
[52] U.S. Cl. ............... 128/662.02; 424/501; 428/402.22
[58] Field of Search ................. 428/402.22; 128/662.02; 424/501

[56] References Cited

U.S. PATENT DOCUMENTS

| | | | |
|---|---|---|---|
| 3,893,980 | 7/1975 | Allcock et al. | 528/321 |
| 4,276,885 | 7/1981 | Tickner et al. | 424/9.52 |
| 4,352,883 | 10/1982 | Lim | 435/178 |
| 4,440,921 | 4/1984 | Allcock et al. | 528/168 |
| 4,442,843 | 4/1984 | Rasor et al. | 424/9.52 |
| 4,495,174 | 1/1985 | Allcock et al. | 424/78.37 |
| 4,592,755 | 6/1986 | Penten et al. | 623/8 |
| 4,657,756 | 4/1987 | Rasor et al. | 424/9.52 |
| 4,681,119 | 7/1987 | Rasor et al. | 424/9.52 |
| 4,718,433 | 1/1988 | Feinstein | 424/9.52 |
| 4,777,154 | 10/1988 | Torobin | 501/84 |
| 4,880,622 | 12/1989 | Allcock et al. | 514/772.3 |
| 4,927,761 | 5/1990 | Reading et al. | 435/178 |
| 4,946,938 | 8/1990 | Magill et la. | 528/399 |
| 4,975,280 | 12/1990 | Schacht et al. | 424/4.28 |
| 4,990,336 | 2/1991 | Silvestri et al. | 424/4.26 |
| 5,053,451 | 10/1991 | Allcock et al. | 524/600 |
| 5,078,994 | 1/1992 | Nair et al. | 424/501 |
| 5,104,947 | 4/1992 | Schacht et al. | 525/538 |
| 5,149,543 | 9/1992 | Cohen et al. | 424/499 |

FOREIGN PATENT DOCUMENTS

| | | |
|---|---|---|
| 0127989 | 12/1984 | European Pat. Off. . |
| 0458745A1/B1 | 11/1991 | European Pat. Off. . |
| 2145992 | 4/1985 | United Kingdom . |
| WO80/02365 | 11/1980 | WIPO . |
| WO92/05778 | 4/1992 | WIPO . |

OTHER PUBLICATIONS

Allain, C. and L. Salome, "Geleaton of Semidilute Polymer Solutions by Ion Complexation: Critical Behavior of the Pheological Properties versus Cross–Link Concentration," *Macromolecules*, 23, pp. 981–987 (1990).
Allcock, et al., "Polyphosphazenes with Etheric Side Groups: Prospective Biomedical and Solid Electrolyte Polymers", *Macromolecules* 19, 1508 (1986).
Allcock, Harry, et al., "Diazo Coupling Catecholamines with Poly(organophosphazenes)." *Macromolecules*, vol. 16(9), p. 1405.
Allcock, et al., "Synthesis of Sugar–Substituted Cyclic and Polymeric Phosphazenes and Their Oxidation Reduction, and Aetrylation Reactions", *Macromolecules* 16, 715 (1983).
Allcock, Harry R., et al., "Covalent Linkage of Proteins to Surface–Modified Poly(organophosphazene): Immobilization of Glucose–6–Phosphate Dehydrogenase and Trypsin," *Macromolecules*, vol. 19(1):1502–1508 (1986).
Allcock, et al., "Glyceryl Polyphosphazenes: Synthesis, Properties, and Hydrolysis", *Macromolecules* 21, 1980 (1988).
Allcock, H. R., et al., "Hydrolysis Pathways for Aminophosphazenes", *Inorg. Chem. 21(2):515–521 (1982)*.
Allcock, H. R., et al., "Phosphonitrillic Compounds, XV, High Molecular Weight Poly[bis(amino)phosphazenes] and Mixed–Substituent Poly(aminophosphazenes)," *Inorg. Chem.* 11, 2584 (1972).
Allcock and Austin, "Schiff Base Coupling of Cyclic and High–Polymeric Phosphazenes to Aldehydes and Amines: Chemotherapeutic Models", *Macromolecules*, vol. 14, p. 1616 (1981).
Allcock, H. R., Gebura, M.; Kwon, S.: Neenan, T. X., "Amphiphilic polyphosphazenes as membrane materials: influence of side group of radiation cross–linking", *Biomaterials*, 9, 500 (1988).
Allcock, Harry R. and Sukky Kwon, "An Ionically Cross–Linkable Polyphophazene: Poly[bix(carboxylatophenoxy)phosphazene] and Its Hydrogels and Membranes", *Macromolecules* 22:75–79 (1989).
Andrianov, Alexander K., et al., "Controlled Release Using Polyphosphazene Hydrogels," *J. Controlled Release* 27:69–77 (1993).
Carroll, B. A., et al., "Ultrasonic Contrast Enhancement of Tissue by Encapsulated Microbubbles," *Radiology*, vol. 143, pp. 747–750 (1982).

(List continued on next page.)

*Primary Examiner*—Peter F. Kulkosky
*Attorney, Agent, or Firm*—Arnall Golden & Gregory

[57] ABSTRACT

Compositions, methods for preparing and methods of using air-filled polymeric microcapsules for ultrasound imaging are disclosed. Air-encapsulating microcapsules are formed by ionotropically gelling synthetic polyelectrolytes such as poly(carboxylatophenoxy)phosphazene, poly(acrylic acid), poly(methacrylic acid) and methacrylic acid copolymers (Eudragit's) by contact with multivalent ions such as calcium ions. In the preferred embodiment, the average size of the microcapsules is less than seven μm so that they are suitable for injection intravenously. The polymeric microcapsules are stable to imaging and display high echogenicity, both in vitro and in vivo. Due to their in vivo stability their potential application is extended beyond vascular imaging to liver and renal diseases, fallopian tube diseases, detecting and characterizing tumor masses and tissues, and measuring peripheral blood velocity. The microcapsules can optionally be linked with ligands that minimize tissue adhesion or that target the microcapsules to specific regions.

20 Claims, No Drawings

OTHER PUBLICATIONS

Carroll, Barbara A., et al., "Gelatin Encapsulated Nitrogen Microbubbles as Ultrasonic Contrast Agents," *Invest. Radiol.*, vol. 15, pp. 260–266 (1980).

Cohen, Smadar, et al., "Ionically Cross–Linkable Polyphosphazene: A Novel Polymer for Microencapsulation," *J. Am. Chem. Soc.* 112:7832–7833 (1990).

de Visser, A. C., et al., "A Biodegradable Drug Delivery System Based on Polyphosphazene," 10th International Symposium on Controlled Release of Bioactive Materials, Jul. 24–27, 1983, Sponsored by Controlled Release Society, Inc.

Feinstein, Steven B., et al., "Contrast Echocardiograhy During Coronary Arteriography in Humas: Perfusion and Anatomic Studies," *J. Am. Coll. Cardiol.* 11, 59–65 (1988).

Feinstein, Steven B., et al., "Two–Dimensional Contrast Echocardiography. I. In Vitro Development and Quantitative Analysis of Echo Contrast Agents," *J. Am. Coll. Cardiol.*, vol. 3, pp. 14–20 (1984).

Fritzsch, Thomas, et al., "Preclinical and Clinical Results with an Ultrasonic Contrast Agent," *Invest. Radiol.* vol. 23 (Suppl 1), pp. 302–305 (1988).

Fritzsch. T., et al., "SH U 508, A Transpulmonary Echocontrast Agent," *Invest. Radiol.*, vol. 25 (Suppl 1), 160–161 (1990).

Gottlieb, S., et al., *J. Am. Soc. Echo*, vol. 3, p. 328 (1990), Abstract*.

Grolleman, C. W. J., et al., "Studies on a Bioerodible Drug Carrier System Based on Polyphosphazene", *J. Controlled Release* 3:143–154 (1986).

Keller, Mark W., et al., "Automated Production and Analysis of Echo Contrast Agents," *J. Ultrasound Med.*, vol. 5, pp. 493–498 (1986).

Kwok, K. K., et al., "Production of 5–15 µm Diameter Alginate–Polylysine Microcapsules by an Air–Atomization Technique", *Pharm. Res.*, vol. 8(3) pp. 341–344 (1991).

Lehman, K. O. R., in "Aqueous polymeric coatings for pharmaceutical dosages forms" Ed. J. W. McGinity, Marcel Dekker, 1989, pp. 1–93.

Rovai, Daniele, et al., "Contrast Echo Washout Curves From the Left Ventricle: Application of Basic Principles of Indicator–Dilution Theory and Calculation of Ejection Fraction," *J. Am. Coll. Cardiol.*, vol. 10, pp. 125–134 (1987).

Schneider, Michel, et al., "Polymeric Microballoons as Ultrasound Contrast Agents," *Invest. Radiol.*, vol. 27, pp. 134–139 (1992).

Shapiro, Janine R., et al., "Intravenous Contrast Echocardiography With Use of Sonicated Albumin in Humans: Systolic Disappearance of Left Ventricular Contrast After Transpulmonary Transmission," *J. Am. Coll. Cardiol.*, vol. 16, pp. 1603–1607 (1990).

Shearwater Polymers, Inc., "Polyethylene Glycol Derivatives," Catalog (1993).

Smith, Mikel, et al., "Left Heart Opacification with Peripheral Venous Injection of a New Saccharide Echo Contrast Agent in Dogs," *J. Am. Coll. Cardiol.*, vol. 13, pp. 1622–1628 (1989).

Wheatley, Margaret A., et al., "Contrast agents for diagnostic ultrasound: development and evaluation of polymer–coated microbubbles," *Biomaterials* 11:713–718 (1990).

Chem. Ab. 93–406825 Jun. 1992, Fritsch et al DE 4219724.

Chem. Ab. 91–281222 May 1991, WO9112823.

Chem. Ab. 92–366002 WO9217212 Oct. 1992.

GAS-FILLED POLYMERIC MICROBUBBLES FOR ULTRASOUND IMAGING

The present application is a continuation-in-part application of U.S. Ser. No. 07/880,248, filed on May 8, 1992, U.S. Pat. No. 5,308,701 by Smadar Cohen, Carmen Bano, Karyn Visscher, Marie Chow, Harry Allcock, and Robert Langer, which is a divisional application of U.S. Ser. No. 07/593,684, filed on Oct. 5, 1990, by Smadar Cohen, Carmen Bano, Karyn Visscher, Marie Chow, Harry Allcock, and Robert Langer, now U.S. Pat. No. 5,149,543.

BACKGROUND OF THE INVENTION

This invention is in the area of polymeric delivery systems, and in particular is polymeric microcapsules that encapsulate gas and methods for their preparation and use.

Diagnostic ultrasound is a powerful, non-invasive tool that can be used to obtain information on the internal organs of the body. The advent of grey scale imaging and color Doppler have greatly advanced the scope and resolution of the technique. Although techniques for carrying out diagnostic ultrasound have improved significantly, there is still a need to enhance the resolution of the imaging for: (i) cardiac, solid organ, and vascular anatomic conduits (for example, the imaging of macrophage activity); (ii) solid organ perfusion; and (iii) Doppler signals of blood velocity and flow direction during real-time imaging.

Traditional, simple ultrasonic echograms reveal blood vessel walls and other echo-producing structures. However, since echoes from blood normally are not recorded, identifying which echoes are from which blood vessels is usually difficult. For example, echoes from the far wall of one blood vessel can be confused with the near wall of an adjacent blood vessel, and vice versa.

Ultrasonic contrast agents can be used to increase the amount of ultrasound reflected back to a detector. Ultrasonic contrast mediums fill the entire intraluminal space with echoes and readily permit identification of the correct pair of echoes corresponding to the walls of a particular blood vessel.

Ultrasonic contrast agents are primarily used in high-flow systems in which the contrast enhancement can be quickly evanescent. For echocardiography, a full display of bubble agents, ranging in size from two μm to 12 μm, and persisting from two or three to 30 seconds, has been used. For other applications, such as neurosonography, hysterosalpingography, and diagnostic procedures on solid organs, the agent must have a lifetime of more than a few circulation times and concentrate in organ systems other than the vascular tree into which it is injected. It must also be small enough to pass through the pulmonary capillary bed (less than eight microns).

Aqueous suspensions of air microbubbles are the preferred echo contrast agents due to the large differences in acoustic impedance between air and the surrounding aqueous medium. After injection into the blood stream, the air bubbles should survive at least for the duration of examination. The bubbles should be injectable intravenously and small enough to pass through the capillaries of the lungs.

The simplest suspension of air bubbles has been obtained by hand agitation of 70% dextrose or sorbitol solutions. However, this method produces large bubbles with an average diameter of greater than 15 μm that exhibit a very limited in vitro stability (less than 1 minute). Feinstein, S. B., et al., *J. Am. Coll. Cardiol., Vol.* 3, pp. 14–20 (1984); Keller, M. W., et al., *J. Ultrasound Med.,* Vol. 5, pp. 493–498 (1986). Smaller bubbles (usually approximately five μm in diameter) have been obtained by sonicating solutions of 50% or 70% dextrose or Renografin-76 (diatrizoate meglumin 66%) but their in vitro persistence still seldom exceeds a few minutes (Feinstein, *J. Am. Coll. Cardiol.* 11, 59–65 (1988), and Keller, (1988)), and their in vivo persistence only a few seconds. This short lifetime may be appropriate for some applications in cardiology but may not be sufficient for organ imaging.

Air-filled particles with a polymeric shell should exhibit a longer persistence after injection than a nonpolymeric microbubble, and may be suitable not only for cardiology but also for organ and peripheral vein imaging. A variety of natural and synthetic polymers have been used to encapsulate imaging contrast agents, such as air. Research efforts in this area have to date primarily focused on agarose and alginate as the encapsulating polymers.

Agarose gel microbeads can be formed by emulsifying agarose-parafilm oil mixtures or through the use of teflon molds. In both cases, temperature-mediated gelation of agarose requires temperature elevations that render difficult the encapsulation gaseous imaging contrast agents.

Alginate, on the other hand, can be ionically cross-linked with divalent cations, in water, at room temperature, to form a hydrogel matrix, as described by Wheatley, et al., *Biomaterials* 11, 713–718 (1990) and Kwok, K. K., et al., *Pharm. Res.,* Vol. 8(3) pp. 341–344 (1991). Wheatley, et al., produced ionically crosslinked microcapsules less that ten microns in diameter, where were formed of alginate, encapsulating air, for use in diagnostic ultrasound. Kwok produced microparticles in the range of 5 to 15 μm by spraying a sodium alginate solution from an air-atomizing device into a calcium chloride solution to effect crosslinking, and then further crosslinking the resulting microcapsules with poly-L-lysine.

Schneider, et al., *Invest. Radiol.,* Vol. 27, pp. 134–139 (1992) described three micron, air-filled polymeric particles. These particles were stable in plasma and under applied pressure. However, at 2.5 MHz, their echogenicity was low. Another drawback of these particles was that organic solvents (tetrahydrofuran and cyclohexane) were used to prepare the particles. Organic solvents can be difficult to remove from the microbubble and may cause a health risk to the patient.

Another type of microbubble suspension has been obtained from sonicated albumin. Feinstein, et al., *J. Am. Coll. Cardiol.,* Vol. 11, pp. 59–65 (1988). Feinstein describes the preparation of microbubbles that are appropriately sized for transpulmonary passage with excellent stability in vitro. However, these microbubbles are short-lived in vivo (T½=few seconds, which is approximately equal to one circulation pass) because of their instability under pressure (Gottlieb, S., et al., *J. Am. Soc. Echo,* Vol. 3, pp. 328 (1990), Abstract; Shapiro, J. R., et al., *J. Am. Coll. Cardiol.,* Vol. 16, pp. 1603–1607 (1990)).

Gelatin-encapsulated air bubbles have been described by Carroll, et al. (Carroll, B. A., et al., *Invest. Radiol.,* Vol. 15, pp. 260–266 (1980); and Carroll, B. A., et al., *Radiology,* Vol. 143, pp. 747–750 (1982)), but due to their large sizes (12 and 80 μm) they would likely not pass through pulmonary capillaries. Gelatin-encapsulated microbubbles have also been described in PCT/US80/00502 by Rasor Associates, Inc. These are formed by "coalescing" the gelatin.

Microbubbles stabilized by microcrystals of galactose (SHU 454 and SHU 508) have also been reported by Fritzsch, T., et al., *Invest. Radiol.* Vol. 23 (Suppl 1), pp. 302–305 (1988); Fritzsch, T., et al., *Invest. Radiol.*, Vol. 25 (Suppl 1), 160–161 (1990). The microbubbles last up to 15 minutes in vitro but less than 20 seconds in vivo (Rovai, D., et al., *J. Am. Coll. Cardiol.*, Vol. 10, pp. 125–134 (1987); Smith, M., et al., *J. Am. Coll. Cardiol.*, Vol. 13, pp. 1622–1628 (1989).

A disadvantage of using natural polymers is that their biocompatibility is variable, and, due to impurities in the preparation extracts, it is difficult to reproduce some properties of the polymer. Synthetic polymers are preferable because they are reproducible and their properties can be tailored to specific needs, including biodegradability.

Synthetic polymers are used increasingly in medical science since they can incorporate specific properties such as strength, hydrogel characteristics, permeability and biocompatability, particularly in fields like cell encapsulation and drug delivery, where such properties are often prerequisites. However, typical methods for the fabrication of synthetic polymers into matrices or drug delivery particles involve heat, which makes encapsulating gaseous imaging contrast agents particularly difficult, or organic solvents, which may be injurious to the health of the patient.

European Patent Application No. 91810366.4 by Sintetica S. A. (0 458 745 A1) discloses air or gas microballoons bounded by an interfacially deposited polymer membrane that can be dispersed in an aqueous carrier for injection into a host animal or for oral, rectal, or urethral administration, for therapeutic or diagnostic purposes. The microballoons are prepared by the steps of: emulsifying a hydrophobic organic phase into a water phase to obtain an oil-in-water emulsion; adding to the emulsion at least one polymer in a volatile organic solvent that is insoluble in the water phase; evaporating the volatile solvent so that the polymer deposits by interfacial precipitation around the hydrophobic phase in the water suspension; and subjecting the suspension to reduced pressure to remove the hydrophobic phase and the water phase in a manner that replaces air or gas with the hydrophobic phase. There are two major disadvantages of this process. First, only polymers that have very specific solubility profiles can be used to prepare the microbubbles, i.e., they must be "interfacially depositable" on a hydrophobic phase in an aqueous medium, and soluble in a volatile organic solvent that is water-insoluble. Second, the process requires the use of organic solvents, which may be hard to completely remove from the microbubble and which may be injurious to the patient's health.

It would be useful to have a method to encapsulate imaging contrast agents with biodegradable or nonbiodegradable synthetic polymers that can be accomplished without the use of elevated temperatures or organic solvents.

Another disadvantage of current microbubble technology is the tendency of the microbubble to adhere to tissues, and the inability to effectively target the microbubbles to specific regions of interest in the body, for example, a solid tumor site or disperse tumor cells. It would be desirable to have a polymeric microbubble that has a surface that minimizes tissue adhesion, or that can be designed to target to specific regions in the body.

It is therefore an object of the present invention to provide gas-filled microcapsules made from synthetic polymers.

It is another object of the present invention to provide a gas-filled microcapsule that can persist for more than a few circulation times.

It is still another object of the present invention to provide a gas-filled microcapsule that can be prepared without the use of heat or organic solvents.

It is a further object of the present invention to provide methods for preparing these microcapsules.

It is still a further object of the present invention to provide gas-filled microcapsules that do not adhere to tissues.

It is yet a further object of the invention to provide gas-filled microcapsules that are targeted to specific regions of the body.

SUMMARY OF THE INVENTION

Gas-filled ionically crosslinked synthetic polymeric microcapsules, and methods for their preparation and use, are disclosed. The gas-filled polymeric microcapsules are useful in diagnostic ultrasound imaging, and can be prepared in micron and submicron sizes that are injectable and that are capable of passing through the pulmonary capillary bed.

The microcapsules are prepared by crosslinking a water-soluble synthetic polymer that contains charged side chains with multivalent ions of the opposite charge. The product, typically a hydrogel, is optionally further stabilized by exposing the product to multivalent polyions, preferably in the form of an ionic polymer, of the same charge as those used to form the hydrogel.

In the preferred embodiment, hydrolytically stable poly-(organophosphazenes) that contain carboxylic acid, sulfonic acid or hydroxyl substituent groups are crosslinked with divalent or trivalent pharmaceutically acceptable cations such as zinc, calcium, bismuth, barium, magnesium, aluminum, copper, cobalt, nickel, or cadmium, and preferably $Ca^{2+}$ or $Al^{3+}$, and then stabilized with a polycation such as poly-L-lysine.

In one embodiment, the poly(organophosphazene) contains (i) ionized or ionizable pendant groups that contain, for example, carboxylic acid, sulfonic acid, or hydroxyl moieties, and (ii) pendant groups that are susceptible to hydrolysis under the conditions of use, to impart biodegradability to the polymer. Suitable hydrolyzable groups include, for example, chlorine, amino acid, amino acid ester, imidazole, glycerol, and glucosyl.

The microcapsules can be targeted to specific regions of the body by covalently binding to the polymer a targeting molecule. The targeting molecule can be, for example, a protein or peptide (such as a hormone, antibody or antibody fragment such as the Fab or $Fab_2$ antibody fragments, or a specific cell surface receptor ligand), lipid, polysaccharide, nucleic acid, carbohydrate, a combination thereof, or other molecule, including a synthetic molecule, that identifies and localizes at the target material.

The microcapsules can also be designed to minimize tissue adhesion by covalently binding a poly(alkylene glycol) moiety to the surface of the microcapsule. The surface poly(alkylene glycol) moieties have a high affinity for water that reduces protein adsorption onto the surface of the particle. The recognition and uptake of the microcapsule by the reticulo-endothelial system (RES) is therefore reduced.

In one embodiment, the terminal hydroxyl group of the poly(alkylene glycol) can be used to covalently attach biologically active molecules, or molecules affecting the charge, lipophilicity or hydrophilicity of the particle, onto the surface of the microcapsule. The biologically active molecule can be a protein, carbohydrate or polysaccharide, nucleic acid, lipid, a combination thereof, or a synthetic molecule, including organic and inorganic materials.

In a preferred embodiment, the microcapsules are prepared by sonicating solutions of synthetic polymer, typically using ultrasonic frequencies of between 5,000 and 30,000 Hz, to produce a highly aerated gassed solution, and spraying the polymer solution into a solution of multivalent ions. Microcapsules produced by this method are typically smaller than seven microns. In a preferred embodiment, the microcapsules have a diameter in the range of between approximately one and seven microns.

DETAILED DESCRIPTION OF THE INVENTION

Synthetic polymers with ionically crosslinkable groups are crosslinked in gasified solutions of ions of the opposite charge to encapsulate gaseous imaging contrast agents. The resulting product is a relatively homogenous population of spherical hydrogel gas-filled microcapsules. As used herein, a "microcapsule" refers to a spherical hydrogel gas-filled particle which may have one or more gas bubbles entrapped therein, and may have a liquid core of the same or different material as the hydrogel.

Ionic crosslinking occurs in solutions of anionic polyelectrolytes and cations, or cationic polyelectrolytes and anions, due to strong electrostatic forces surrounding the polymeric chains. The formation and properties of polymers crosslinked via polyvalent ions depend on the properties, concentrations, and distribution of the ions and the polymer. Polymer chains crosslink via cations or anions by forming complexes liganded with more than one polymer group, creating intramolecular and/or intermolecular crosslinks (C. Allain and L. Salome, *Macromolecules*, Vol. 23, pp. 981–987 (1990).

In the preferred embodiment, sterilized air is encapsulated within hydrogel microspheres which are subsequently further crosslinked and can be converted into microcapsules by liquefying the core hydrogel.

The method for making the microcapsules does not require the use of non-water-miscible organic solvents, is highly reproducible and requires few processing steps. Synthetic polymers are selected that are biocompatible, and are at least partially soluble in aqueous solutions, or which form a dispersion in an aqueous solution. In a preferred embodiment, the synthetic polymer is biodegradable over a short period of time, usually a few days to one week. The rate of hydrolysis of the polymer can typically be manipulated so that it can be processed and remain intact for a desired period of time.

In a preferred embodiment, microcapsules exhibit an in vivo lifetime of from approximately thirty seconds to thirty minutes or more, or at least enough time to be delivered to the region of interest and for the ultrasound operator to carry out the diagnostic tests.

I. Selection, Synthesis, Crosslinking, and Modification of Water-soluble Polyelectrolyte Polymers A number of polymers can be used to form the crosslinked hydrogel. In general, polymers that are suitable are those that have charged side groups and are at least partially soluble in aqueous solutions, such as water, buffered salt solutions, or aqueous alcohol solutions, or a monovalent ionic salt thereof. As used herein, "partially soluble" refers to a polymer that is soluble to the extent of at least 0.001 percent by weight of aqueous solution, and preferably, soluble to an extent of at least 0.01 percent by weight.

Examples of polymers with acidic side groups that can be reacted with cations include those with carboxylic acid, sulfonic acid, sulfamic acid, phosphoric acid, phosphonic acid, hydroxyl or thiol groups with acidic hydrogens (for example, halogenated, preferably fluorinated, alcohols), boric acid, or any other moiety that will react with a cation to form a conjugate base. Examples include poly(organophosphazenes) with acidic substituent groups, poly(acrylic acids), poly(methacrylic acids), copolymers of acrylic acid and methacrylic acid, copolymers of vinyl acetate with acidic monomers, sulfonated polymers, such as sulfonated polystyrene, and copolymers formed by reacting acrylic or methacrylic acid and vinyl ether monomers or polymers.

Examples of polymers with basic side groups that can be reacted with anions include those that have amino, imino, mono- or di-(alkyl or aryl)amino, heterocyclic nitrogen, or quaternary amino groups, and specifically include poly(vinyl amines), poly(vinyl pyridine), poly(vinyl imidazole), poly(vinyl pyrrolidone) and some amino or substituted polyphosphazenes. The ammonium quaternary salt of the polymers can also be formed from the backbone nitrogens or pendant imino groups.

A. Synthesis and Selection of Polymers

1. Polyphosphazenes.

Polyphosphazenes are polymers with backbones consisting of alternating phosphorus and nitrogen, separated by alternating single and double bonds. Each phosphorous atom is covalently bonded to two pendant groups ("R"). The repeat unit in polyphosphazenes has the following general formula:

wherein n is an integer.

The substituent ("R") can be any of a wide variety of moieties that can vary within the polymer, including but not limited to aliphatic, aryl, aralkyl, alkaryl, carboxylic acid, heteroaromatic, carbohydrates, including glucose, heteroalkyl, halogen, (aliphatic)amino- including alkylamino-, heteroaralkyl, di(aliphatic)amino- including dialkylamino-, arylamino-, diarylamino-, alkylarylamino-, -oxyaryl including but not limited to -oxyphenyl$CO_2H$, -oxyphenyl$SO_3H$, -oxyphenylhydroxyl and -oxyphenyl$PO_3H$; -oxyaliphatic including -oxyalkyl, -oxy(aliphatic)$CO_2H$, -oxy(aliphatic)$SO_3H$, -oxy(aliphatic)$PO_3H$, and -oxy-(aliphatic)hydroxyl, including -oxy(alkyl)hydroxyl; -oxyalkaryl, -oxyaralkyl, -thioaryl, -thioaliphatic including -thioalkyl, -thioalkaryl, -thioaralkyl, —NHC(O)O-(aryl or aliphatic), —O—[($CH_2)_xO]_y$—$CH_2)_xNH_2$, —O—[($CH_2)_xO]_yCH_2)_xNH(CH2)_xSO_3H$, and —O—[($CH_2)_xO]_y$-(aryl or aliphatic), wherein x is 1–8 and y is an integer of 1 to 20. The groups can be bonded to the phosphorous atom through, for example, an oxygen, sulfur, nitrogen, or carbon atom. The polymers can be designed to be hydrophobic, amphophilic, or hydrophilic; water-stable or water-erodible; crystalline or amorphous; or bioinert or bioactive.

The term amino acid, as used herein, refers to both natural and synthetic amino acids, and includes, but is not limited to alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl.

The term amino acid ester refers to the aliphatic, aryl or heteroaromatic carboxylic acid ester of a natural or synthetic amino acid.

The term alkyl, as used herein, refers to a saturated straight, branched, or cyclic hydrocarbon, or a combination thereof, typically of $C_1$ to $C_{20}$, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, 2,3-dimethylbutyl, heptyl, octyl, nonyl, and decyl.

The term (alkyl or dialkyl)amino refers to an amino group that has one or two alkyl substituents, respectively.

The terms alkenyl and alkynyl, as used herein, refers to a $C_2$ to $C_{20}$ straight or branched hydrocarbon with at least one double or triple bond, respectively.

The term aryl, as used herein, refers to phenyl or substituted phenyl, wherein the substituent is halo, alkyl, alkoxy, alkylthio, haloalkyl, hydroxyalkyl, alkoxyalkyl, methylenedioxy, cyano, C(O)(lower alkyl), —$CO_2H$, —$SO_3H$, —$PO_3H$, —$CO_2$alkyl, amide, amino, alkylamino and dialkylamino, and wherein the aryl group can have up to 3 substituents.

The term aliphatic refers to hydrocarbon, typically of $C_1$ to $C_{20}$, that can contain one or a combination of alkyl, alkenyl, or alkynyl moieties, and which can be straight, branched, or cyclic, or a combination thereof.

The term halo, as used herein, includes fluoro, chloro, bromo, and iodo.

The term aralkyl refers to an aryl group with an alkyl substituent.

The term alkaryl refers to an alkyl group that has an aryl substituent, including benzyl, substituted benzyl, phenethyl or substituted phenethyl, wherein the substituents are as defined above for aryl groups.

The term heteroaryl or heteroaromatic, as used herein, refers to an aromatic moiety that includes at least one sulfur, oxygen, or nitrogen in the aromatic ring, and that can be optionally substituted as described above for aryl groups. Nonlimiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbozolyl, oxazolyl, thiazolyl, isothiazolyl, 1,2,4-thiadiazolyl, isooxazolyl, pyrrolyl, pyrazolyl, quinazolinyl, pyridazinyl, pyrazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, and pyrazolopyrimidinyl.

The term heteroalkyl, as used herein, refers to a alkyl group that includes a heteroatom such as oxygen, sulfur, or nitrogen (with valence completed by hydrogen or oxygen) in the carbon chain or terminating the carbon chain.

In one embodiment, the poly(organophosphazene) contains (i) ionized or ionizable pendant groups, and (ii) pendant groups that are susceptible to hydrolysis under the conditions of use, to impart biodegradability to the polymer. Suitable hydrolyzable groups include, for example, chlorine, amino acid, amino acid ester, imidazole, glycerol, and glucosyl.

The degree of hydrolytic degradability of the polymer will be a function of the percentage of pendant groups susceptible to hydrolysis and the rate of hydrolysis of the hydrolyzable groups. The hydrolyzable groups are believed to be replaced by hydroxyl groups in aqueous environments to provide P—OH bonds that impart hydrolytic instability to the polymer.

While the acidic or basic groups are usually on nonhydrolyzable pendant groups, they can alternatively, or in combination, also be positioned on hydrolyzable groups.

In a typical embodiment, a portion, generally 10% or less, of the side chain groups (the R groups in formula 1), are susceptible to hydrolysis.

Specific examples of hydrolyzable side chains are unsubstituted and substituted imidizoles and amino acid esters in which the group is bonded to the phosphorous atom through an amino linkage (polyphosphazene polymers in which both R groups are attached in this manner are known as polyaminophosphazenes).

In polyimidazolephosphazenes, some of the "R" groups on the polyphosphazene backbone are imidazole rings, attached to phosphorous in the backbone through a ring nitrogen atom. Other "R" groups can be organic residues that do not participate in hydrolysis, such as methyl phenoxy groups or other groups shown in Allcock, at al., *Macromolecule* 10:824–830 (1977), hereby incorporated by reference.

Specific examples of R groups that are not capable of hydrolysis are alkyl, aralkyl, or aryl group having 20 carbon atoms or less (more preferably 12 carbon atoms or less); or a heteroalkyl or heteroaryl group having 20 or less carbons and heteroatoms (more preferably 12 or less carbon or heteroatoms). If the alkyl chain is too long, the polymer will be totally insoluble in water. The groups can be bonded to the phosphorous atom through e.g., an oxygen, sulfur, nitrogen, or carbon atom.

In general, when the polyphosphazene has more than one type of pendant group, the groups will vary randomly throughout the polymer, and the polyphosphazene is thus a random copolymer. Phosphorous can be bound to two like groups, or two different groups. Polyphosphazenes with two or more types of pendant groups can be produced by reacting poly(dichlorophosphazene) with the desired nucleophile or nucleophiles in a desired ratio. The resulting ratio of pendant groups in the polyphosphazene will be determined by a number of factors, including the ratio of starting materials used to produce the polymer, the temperature at which the nucleophilic substitution reaction is carried out, and the solvent system used. While it is very difficult to determine the exact substitution pattern of the groups in the resulting polymer, the ratio of groups in the polymer can be easily determined by one skilled in the art.

It should be understood that certain groups, such as heteroaromatic groups other than imidazole, hydrolyze at an extremely slow rate under neutral aqueous conditions, such as that found in the blood, and therefore are typically considered nonhydrolyzable groups for purposes herein. However, under certain conditions, for example, low pH, as found, for example, in the stomach, the rate of hydrolysis of normally nonhydrolyzable groups (such as heteroaromatics other than imidazole) can increase to the point that the biodegradation properties of the polymer can be affected. One of ordinary skill in the art using well known techniques can easily determine whether pendant groups hydrolyze at a significant rate under the conditions of use. One of ordinary skill in the art can also determine the rate of hydrolysis of the polyphosphazenes of diverse structures as described herein, and will be able to select the polyphosphazene that provides the desired biodegradation profile for the targeted use.

The term biodegradable polymer refers to a polymer that degrades within a period that is acceptable in the desired application, less than weeks or months, when exposed to a physiological solution of pH between 6 and 8 having a temperature of between about 25° C. and 37° C.

Polyphosphazenes can be made by displacing the chlorines in poly(dichlorophosphazene) with a selected substituent group or groups. Desired proportions of hydrolyzable to nonhydrolyzable side chains in the polymer can be achieved by adjusting the quantity of the corresponding nucleophiles that are reacted with poly(dichlorophosphazene). The preferred polyphosphazenes have a molecular weight of over 1,000.

Methods for synthesis of polyphosphazenes are described by Allcock, H. R.; et al., *Inorg. Chem.* 11, 2584 (1972); Allcock, et al., *Macromolecules* 16, 715 (1983); Allcock, et al., *Macromolecules* 19, 1508 (1986); Allcock, H. R.; Gebura, M.; Kwon, S.; Neenan, T. X. *Biomaterials*, 19, 500 (1988); Allcock, et al., *Macromolecules* 21, 1980 (1988); Allcock, et al., *Inorg. Chem.* 21(2), 515–521 (1982); Allcock, et al., *Macromolecules* 22, 75 (1989); U.S. Pat. Nos. 4,440,921, 4,495,174 and 4,880,622 to Allcock, et al.; U.S. Pat. No. 4,946,938 to Magill, et al., and Grolleman, et al., *J. Controlled Release* 3, 143 (1986), the teachings of which are specifically incorporated herein. The synthesis of ionically crosslinkable poly(biscarboxylatophenoxy-)phosphazene, and the preparation of hydrogels from this polymer, is taught in U.S. Pat. No. 5,053,451. Other patents on poly(organophsphazenes) include U.S. Pat. Nos. 4,440, 921, 4,880,622, 3,893,980, 4,990,336, 4,975,280, 5,104,947, and 4,592,755.

Most preferably, the polyphosphazene is a high molecular weight, water-soluble anionic polyphosphazene, in which a majority of side groups in phosphazene polyelectrolytes are ionic. Carboxylic acid groups are an example of preferred ionic groups.

One example of a preferred polyanionic phosphazene is poly[bis(carboxylatophenoxy)phosphazene (PCPP).

2. Other water soluble polymers with charged side groups.

A wide variety of water soluble or dispersible polymers with ionic side groups are known or can be easily designed by one of ordinary skill in the art of polymer synthesis. The polymers are in general those that are biocompatible, optionally biodegradable, and have acidic or basic substituent groups as described in detail above. The polymers can include nonionic monomers that impart desired properties to the polymer. The polymer can be a condensation polymer or addition polymer. Nonlimiting examples of monomers that can be included in condensation polymers are hydroxyacids such as lactic acid, glycolic acid, and hydroxybutyric acid, and dicarboxylic acids. Biodegradable polymers include those that degrade enzymatically and those that degrade hydrolytically.

Methods for synthesizing the other polymers described above are known to those skilled in the art. See, for example *Concise Encyclopedia of Polymer Science* and *Polymeric Amines and Ammonium Salts*, E. Goethals, editor (Pergamen Press, Elmsford, N.Y. 1980). Many, such as poly(acrylic acid), are commercially available.

One preferred polymer is poly(meth)acrylic acid (wherein the term (meth) acrylic refers to either polymethacrylic acid or polyacrylic acid) or a copolymer of methacrylic acid or acrylic acid with another unsaturated monomer that can be ionic or nonionic. Pharmaceutical applications of poly-(meth)acrylic acids are well known [K. O. R. Lehman in "Aqueous polymeric coatings for pharmaceutical dosages forms" Ed. J. W. McGinity, Marcel Dekker, 1989, pp. 1–93]. Because of its excellent biocompatibility, poly(meth)acrylic acid and copolymers of (meth)acrylic acid are used for artificial implants, dental prosthesis, contact lenses, ointments and coatings for gastroresistant-enterosoluble formulations.

Examples of anionic poly(meth)acrylic acids include but are not limited to copolymers of methacrylic acid and ethyl acrylate poly[ (methacrylic acid)-co-(ethyl acrylate)], also known as Eudragit. The chemical compositions of commercially available polymers (Eudragit L and S) are shown below.

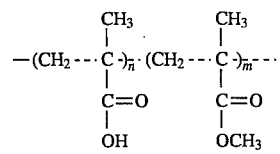

The ratio of the free carboxyl groups to the ester groups is approximately 1:1 in Eudragit L and approximately 1:2 in Eudragit S. The mean molecular weight is calculated from viscosity measurement and equal to 135,000 Da. The polymers correspond to USP/NF, "Methacrylic Acid Copolymer, Type A" (Eudragit L) or "Type B" (Eudragit S). The copolymers are practically insoluble in water, but soluble in 1N sodium hydroxide solution (upon neutralization of carboxyl groups) to give clear to slightly opalescent solutions.

B. Crosslinking the Polymers with Multivalent Ions to Form a Hydrogel

The water-soluble polymer with charged side groups is crosslinked by reacting the polymer with an aqueous solution containing multivalent ions of the opposite charge, either multivalent cations if the polymer has acidic side groups or multivalent anions if the polymer has basic side groups.

The term "pharmaceutically acceptable cation" refers to an organic or inorganic moiety that carries a positive charge that can be administered in vivo without undue toxicity to the host.

The term polyelectrolyte, as used herein, refers to a polymer with ionic side groups.

1. Cross-linking the polymers with acidic side groups by multivalent cations.

The preferred cations for cross-linking the polymers with acidic side groups to form a hydrogel are divalent and trivalent cations such as copper, calcium, aluminum, magnesium, strontium, barium, and tin, although di-, tri- or tetra-functional organic cations such as salts of nitrogenous bases, for example, alkylammonium salts, such as piperidine dihydrochloride, the salt of ethylene diamine tetra(acetic acid), can also be used. Aqueous solutions of the salts of these cations are added to the polymers to form soft, highly swollen hydrogels and membranes. The higher the concentration of cation, or the higher the valence, the greater the degree of polymer cross-linking. Concentrations as low as 0.005M have been demonstrated to crosslink the polymer. Higher concentrations are limited by the solubility of the salt.

2. Cross-linking the polymers with basic side groups with multivalent anions.

The preferred anions for cross-linking the polymers to form a hydrogel are divalent and trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

C. Crosslinking the Polymers with Multivalent Polyions to Form a Semi-Permeable Membrane In some embodiments, additional surface groups on the hydrogel polymer are reacted with polyions of opposite charge to form a semi-permeable membrane on the surface of the hydrogel. The complexed polymer is stable and forms a semipermeable membrane on the microcapsules. The permeability of this membrane for a given entity depends on the molecular weight of the polyion. When the hydrogel is in the form of a microcapsule (or microsphere), the core hydrogel can then be liquified by removing the multivalent ions, for example, by dialysis or addition of a chelating agent.

1. Multivalent polycations useful for crosslinking.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. A preferred polycation is poly(L-lysine). Examples of synthetic polyamines include but are not limited to polyethyleneimine, poly(vinylamine), and poly(allyl amine). There are also natural polycations, such as the polysaccharide chitosan, but these are not preferred.

2. Multivalent polyanions useful for crosslinking polymers with basic side groups.

Polyanions that can form a semi-permeable membrane by reacting with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups.

D. Modification of Acidic Groups on the Polymer Backbone

1. Coupling of Molecules to modify the surface or to target the microcapsule.

The ionically crosslinkable groups on the polymer can be modified by covalently coupling a poly(alkylene glycol) such as poly(ethylene glycol), proteins, peptides, oligosaccharides, carbohydrate, lipids, nucleotide sequences or other molecules to target the microcapsules to specific regions of the body or to certain cell types, or minimize tissue adhesion or uptake by the reticuloendothelial system (RES). The targeting molecule can be, for example, a protein or peptide such as a hormone, antibody or antibody fragment such as the Fab or $Fab_2$ antibody fragments, or a specific cell surface receptor ligand that localizes at the target material.

2. Methods for coupling molecules to the microcapsules.

The coupling involves forming ester, thioester, amide, or sulfamide linkages. Coupling hydroxy, thio, or amine groups with carboxy or sulfoxy groups is known to those skilled in the art.

The polymers can contain various functional groups, such as hydroxy, thio, and amine groups, that can react with a carboxylic acid or carboxylic acid derivative under the coupling conditions. Reactive functional groups not involved in the coupling chemistry must be protected to avoid unwanted side reactions. After the carboxylic acid or derivative reacts with a hydroxy, thio, or amine group to form an ester, thioester, or amide group, any protected functional groups can be deprotected by means known to those skilled in the art.

The term "protecting group" as used herein refers to a moiety which blocks a functional group from reaction, and which is cleavable when there is no longer a need to protect the functional group. Suitable protecting groups for the hydroxyl group include, but are not limited to, certain ethers, esters and carbonates (Greene, T. W. and Wuts, P. G. M., "Protective groups in organic synthesis," John Wiley, New York, 2nd Ed. (1991)). Suitable protecting groups for the carboxyl group include, but are not limited to, those described in Green and Wuts, Protecting Groups in Organic Synthesis, John Wiley (1991). Side-chain functionalities such as carboxylic acids, alcohols, and amines may interfere with the coupling chemistry and must be appropriately protected.

As used herein, "side-chain functionality" refers to functional groups, such as hydroxy, thio, amine, keto, carboxy, alkenyl, alkynyl, carbonyl, and phosphorus derivatives such as phosphate, phosphonate and phosphinate in the polymer or material to be covalently attached to the polymer, that is not involved in coupling to form an ester, thioester, amide or sulfamide bond. Examples of suitable protecting groups are well known to those skilled in the art. See, generally, Greene and Wuts, Protecting Groups in Organic Chemistry, John Wiley (1991).

Examples of protecting groups for amine groups include, but are not limited to, t-butyloxycarbonyl (Boc), benzyloxycarbonyl (Cbz), o-nitrobenzyloxycarbonyl, and trifluoroacetamide (TFA).

3. Coupling other groups on the polymer with biological materials

Amine groups on a polymer backbone can be coupled with amine groups on a peptide by forming a Schiff base, using coupling agents such as glutaraldehyde. An example of this coupling is described by Allcock, et al., *Macromolecules*, Vol. 19(6), pp. 196 (1986), hereby incorporated by reference. In this example, trypsin was bound to amine groups on a polyphosphazene. An aminophenoxy polyphosphazene and trypsin were added to a buffer solution. Glutaric dialdehyde was added to the solution, and the solution was kept at 0° C. for 20 hours.

The amount of bound trypsin was determined by washing the excess trypsin from the polymer, using Lowry protein measurement to determine the amount of unbound trypsin, and calculating the amount of bound trypsin by difference.

Amine groups can also be coupled with DCC or other dehydrating agents, as described above, with carboxy groups on amino acids, proteins or peptides.

Alternatively, one can incorporate amino acids, proteins, or peptides into the polymer backbone by displacing chlorines on chlorine-containing polyphosphazenes, such as polydichlorophosphazene. Since the carboxylate salt of carboxy groups can also displace the chlorine, the carboxy groups must be protected. Examples of this chemistry are described by Alcock, et al., *Macromolecules*, Vol. 10(4), pp. 824–831 (1977), hereby incorporated by reference.

Additionally, amine groups can be converted to diazonium salts, which can be reacted with amine or hydroxy groups on biological materials. An example of this coupling is described by Allcock, et al., *Macromolecules*, Vol. 16(9), pp. 1405 (1983), hereby incorporated by reference.

For example, poly(15% 4-aminophenoxy/85% phenoxy) phosphazene is dissolved in THF containing HCl, and the solution cooled to 0° C. A solution of $NaNO_2$ is added to form the diazonium salt. A buffered solution of d,l-epinephrine is added, and the reaction proceeded in the dark, at 0° C., for 14 hours. A 60% yield is obtained.

Phenol or alcohol substituents on the polymer can be coupled with carboxylic or sulfonic acid groups on biological materials, such as a carboxy group on an amino acid, protein or peptide. The conditions for these coupling reactions are described above.

Aldehyde groups on polymers can be coupled with amines, as described above, by forming a schiff base. An example of this coupling is described by Allcock and Austin, *Macromolecules, Vol.* 14, pp. 1616 (1981), hereby incorporated by reference.

For example, Hexakis(4-aminophenoxy) cyclotriphosphazene (1 gram, 1.2 mmol) is dissolved in diethylene glycol (35 mL), and 16 mmol citral is added. The mixture is stirred at 25° C. for 2 hours, HCl (18 mmol) is added, and the solution is warmed. Additional citral (15 mmol) is added. After 15 minutes at room temperature, 10 mL of water are added. After workup and recrystallization, the resulting yield is 88%.

II. Methods of Making Microcapsules

The method of preparing the microcapsules should be selected to provide a microcapsule having the desired size for the intended use. In a preferred embodiment for the preparation of injectable microcapsules capable of passing through the pulmonary capillary bed, the microcapsules should have a diameter of between approximately one and seven microns. Larger microcapsules may clog the pulmonary bed, and smaller microcapsules may not provide sufficient echogenicity. Larger microcapsules may be useful for administration routes other than injection, for example oral (for evaluation of the gastrointestinal tract) or by inhalation.

A. Preparation of a Polymer Solution

In general, the polymer is dissolved or dispersed into a solution which is then sprayed into a solution of crosslinking counterions. This is typically an aqueous solution or dispersion that can include water-miscible organic solvents, including but not limited to dialkyl sulfoxides, such as dimethyl sulfoxide DMSO); dialkyl formamides, such as dimethyl formamide (DMF); $C_{1-5}$ alcohols, such as methanol and ethanol; ketones such as acetone and methyl ethyl ketone; and ethers such as tetrahydrofuran (THF), dibutyl ether and diethyl ether. The solution can be neutral, acidic or basic, and can contain salts or buffers. If the ionic polymer is insoluble in water, or insufficiently dispersible, the polymer can be converted to its conjugate acid or base that is typically more water soluble, and that conjugate acid or base then exposed to the di- or multivalent counterion for crosslinking.

B. Gases to be Encapsulated

The ratio of polymer to gas is determined based on the gas that is to be encapsulated, for example, as required to produce a particle size small enough to be injected. Any desired inert gas can be incorporated into the polymeric materials at the time of hydrogel formation, including air, argon, nitrogen, carbon dioxide, nitrogen dioxide, methane, helium, neon, and oxygen. Sterilized air or oxygen is a preferred imaging contrast agent.

C. Atomization of Polymer Solution into a Crosslinking Solution

There are at least two methods for the preparation of injectable microcapsules. In one method, a jet head is used that allows the coextrusion of a solution of polymer and air to produce nascent microencapsulated air bubbles which fall into a hardening solution of counterions. A second method employs ultrasound to introduce cavitation-induced bubbles into the polymer before capsule formation by spraying. To incorporate gases other than air, a solution of the desired polymer is placed in an atmosphere of the desired gas and sonicated for a sufficient amount of time before crosslinking to ensure that gas bubbles are dispersed throughout the microparticulates. In either case, the determining factors on size of resulting microcapsules will be the selection and concentration of polymer and solvent, and size of droplets formed by the atomizer.

1. Preparation of one to ten micron Microcapsules

An example of an air-atomizing device is a Turbotak, from Turbotak, Inc., Waterloo, Ontario. A Turbotak is a hollow stainless steel cylinder, 2.64 cm. wide×4 cm. long. Liquid is fed into the Turbotak from the top and pressurized air is fed from the side. The pressurized air mixes with the liquid, forcing tiny liquid droplets out through the orifice of the nozzle. The air pressure can be set to between 50 and 80 psig. The distance between the orifice of the Turbotak and the pan containing the crosslinking ions is fixed at between about one to two feet. The size of the nozzle orifice is 1 to 2 mm in diameter.

Air can be pressurized with a syringe pump such as a Razel pump, having a flow rate in the range of between 5 ml/hr and 30 ml/hr or a Sage pump, having a flow rate in the range of between 0.02 ml/min and 126 ml/min.

Mixing pressurized air with a polymer solution aerates the polymer solution and produces a high yield of air-encapsulated polymeric microcapsules. Even without sonicating the polymer solution, microcapsules produced using the Turbotak nozzle have entrapped air, as seen by light microscopy.

2. Method for the Preparation of larger Microcapsules

Larger microcapsules can be prepared using a droplet-forming apparatus by spraying an aqueous solution of polymer containing the gas of interest through an apparatus such as a plastic syringe, where the polymer solution is extruded through a needle located inside a tube through which air flows at a controlled rate.

The rate of polymer extrusion is controlled, for example, by a syringe pump. Droplets forming at the needle tip are forced off by the coaxial air stream and collected in the crosslinking solution, usually an aqueous solution of bi- or trivalent ions, where they cross-link and are hardened, for example, for between 15 and 30 minutes.

The shape and size of these microcapsules depend on the polymer and cross-linker concentrations and parameters such as the polymer extrusion rate, air flow, and needle diameters used in the microencapsulation procedure.

A typical example for microcapsule preparation utilizes PCPP polymer concentrations of between 1 and 5% (w/v), preferably around 2.5%, and calcium chloride concentrations of between 3 and 7.5% (w/v), preferably 7.5%, respectively. Polymer extrusion rates are between 50 and 100 mL/hour, preferably 70 mL/hour. Air flow rates are in the range of 5 L/hour. Needle diameters of between 18 and 26 gauge (G), preferably around 20 gauge, are used. Using the preferred conditions, the resultant microcapsules are spherical with diameters in the range of 400–700 microns. In general, microcapsules as small as 30 μM can be prepared using this technique.

Macrospheres with millimeter diameters can be prepared by extruding the polymer through pasteur pipets or their equivalent.

D. Processing the Polymeric Microcapsules to Liquify the Core

The polyionic-coated hydrogel microcapsules are collected and further treated with buffer to remove the uncomplexed multivalent ions. For example, to remove uncomplexed multivalent cations, microcapsules can be treated with 0.9% (w/v) KCl with the pH adjusted to around 8.0. The KCl solution dissolves the internal gel, without affecting the external membrane. Other methods can also be used to liquefy the internal gel, including using chelators such as EDTA and sodium citrate.

III. Detecting Gas-Encapsulating Microcapsules

The relatively homogenous population of spherical gel microcapsules, filled with air bubbles, can be seen by an inverted microscope. Most microcapsules produced by the first method are smaller than seven microns in diameter. Particle size analysis can be performed on a Coulter counter.

Due to their in vivo stability their potential application is extended beyond vascular imaging to liver and renal diseases, fallopian tube diseases, detecting and characterizing tumor masses and tissues, and measuring peripheral blood velocity. The microcapsules can optionally be linked with ligands that minimize tissue adhesion or that target the microcapsules to specific regions.

The method for imaging by detection of gas bubbles in a patient uses a transducer which produces pulses, illustrative of ultrasonic acoustic energy, having predetermined frequency characteristics. A first pulse has an increasing frequency with time, and a second pulse has a decreasing frequency with time. Imaging arrangements produce images of the region within the specimen after exposure to the first and second pulses.

The conventional technique for determining the presence of bubbles in the blood stream uses a Doppler shift in the frequency of the ultrasonic acoustic energy which is reflected by the blood. The amplitude of the Doppler bubble signal increases nearly proportionally with increases in the radius of the bubble. The human hearing mechanism is considered the most accurate processor for recognizing whether bubble signals are present or absent. For this reason, it is preferable to have a skilled operator to obtain satisfactory results using Doppler blood flow monitoring equipment.

To determine whether the air-filled microcapsules are useful for in vivo imaging, the following in vitro method, described in more detail in the following examples, can be used.

Microparticles prepared by the above methods are suspended in a capped tissue culture tube. For ultrasound imaging, the tubes are placed on top of a pad covered with coupling medium above the transducer. The transducer is held in place at roughly a 90° angle of incidence to minimize any motion artifacts. The transducer acts as a transmitter and also receives ultrasound radiation scattered back from the tube. B-mode and Doppler images are established for tubes filled with polymeric microcapsules and the resulting images are compared with a control consisting of an image from a tube containing buffer alone. The B-mode of display gives a two dimensional image of a slice through the scanned tube.

This method was used to obtain in vitro results on the microparticles in the working examples described below. These results correlated well with the in vivo results, as shown by Doppler imaging techniques (described below). Since the in vitro and in vivo data showed a high degree of correlation in the working examples, this test is reasonably predictive of the in vivo stability of microparticles.

The methods and compositions described above will be further understood with reference to the following non-limiting examples.

EXAMPLE 1

Preparation of One to Ten Micron Eudragit S 100 Microcapsules

The microencapsulation procedure, optimized to produce microcapsules in the size range of 1–10 μm, is as follows:

Preparation of Eudragit S 100 (5% w/v) Solution 1 gram of S 100 was dissolved overnight, at room temperature, with stirring in 1N KOH, such that the carboxylic acid groups were neutralized. This required adding approximately 190 mg of KOH per gram of S 100. The solution was then diluted with double-distilled water to give a final polymer concentration of 5% (w/v) and solution pH around 7.0 (due to polymer neutralization). If the pH was greater than 7.0, the pH was adjusted with 1N HCl.

Preparation of S 100 Microcapsules

A solution of Eudragit S 100 (5% w/v) containing 0.2% Tween 20 was sonicated with a horn sonicator (output 8, for 15 minutes, in an ice-bath) to produce a gassed S 100 solution that was highly aerated and stable for hours. The gassed solution was extruded from a syringe pump (Razel Instrument) at 150 μl min into an air-atomizing device (Turbotak, Turbotak, Inc., Waterloo, Ontario) and sprayed into a pan containing 250 mL of 15% calcium chloride solution with 0.5% Tween 20.

Upon contact with calcium chloride solution, S 100 was cross-linked by the divalent calcium ions to produce a relatively homogenous population of spherical gel microcapsule, filled with air bubbles. The presence of air bubbles was shown by looking at the microcapsule through an inverted microscope. Most S100 microcapsules were smaller than 7 μm. The yield of microcapsule after one passage through a 7 μm spectrum filter (polyester-based filter, Spectrum) was more than 90%. Particle size analysis (Coulter counter) gave the following number of particles: 90% of the particles were smaller than 5,448 μm, 75% were smaller than 3.763 μm, 50% were smaller than 2.692 μm, 25% were smaller than 2,058 μm, and 10% were smaller than 1.715 μm. Analysis also indicated that 25% of total particle volume belonged to particles with diameter less than 7.65 μm.

EXAMPLE 2

Preparation of PCPP Microcapsules

Preparation of PCPP (2.5% w/v)

100 mg of PCPP were dissolved in 1 mL 30 mg/mL $Na_2CO_3$ (overnight, at room temperature, stirring) and then diluted with phosphate-buffered saline (PBS), pH 7.4 to give a final polymer concentration of 2.5% (w/v) and solution pH of 7.4 (due to polymer deprotonation), if not, the pH was adjusted with 1N HCl.

Preparation of PCPP Microcapsules

A solution of PCPP (2.5% w/v) containing 0.2% Tween 20 was sonicated with a horn sonicator (output 8, for 5 minutes, in an ice-bath) to produce a gassed PCPP solution that was highly aerated and stable for hours. The gassed solution was extruded from a syringe pump (Razel Instrument) at 150 µl/min into an air-atomizing device (Turbotak, Turbotak, Inc., Waterloo, Ontario) and sprayed into a pan containing 250 mL of 7.5% calcium chloride solution containing 0.5% Tween 20. Upon contact with calcium chloride solution, PCPP was crosslinked by the divalent calcium ions to produce a relatively homogenous population of spherical gel microcapsule, filled with air bubbles. The presence of air bubbles in the microcapsule was shown by looking at the microcapsule through an inverted microscope. Particle size analysis (Coulter counter) gave the following number of particles: 90% of the particles were smaller than 14.77 µm, 75% were smaller than 9,253 µm, 50% were smaller than 5.84 µm, 25% were smaller than 4.166 µm, and 10% were smaller than 3,372 µm. Analysis also indicated that 10% of total particle volume belonged to particles with diameter less than 14.57 µm.

EXAMPLE 3

In vitro Ultrasound Imaging

Air-filled microcapsules, at a concentration of $1\times10^6$ particles/mL, were suspended in a capped tissue culture tube with a length of 15 cm. and a depth of 1.5 cm. For ultrasound imaging, the tubes were placed on top of a pad containing a transducer, with coupling medium above the transducer. The transducer was held in place at a 90° angle of incidence to minimize any motion artifacts. B-mode and Doppler images were established for a tube filled with polymeric microcapsules and the resulting images were compared with a control consisting of an image from a tube that contained buffer alone.

A comparison was made between the B-mode sector images of tubes filled with saline and tubes filled with S 100 microcapsules (3–5 µm in diameter) and with PCPP microcapsules (3–5 µm in diameter), respectively.

The brightness seen at the bottom of the picture of the tube filled with saline reflects the saline/air interface within the tube. No echo was returned from the inside of the tube. In the tubes filled with both types of polymeric microcapsules, a very strong echo was returned to the transducer, giving a clear image of the tube, and demonstrating that the polymeric microcapsules were highly echogenic. The polymeric microcapsules were still highly echogenic, 24 hours and a week after preparation (during which they were kept at room temperature), as verified by subsequent B-mode images.

EXAMPLE 4

In vivo Ultrasound Imaging

In vivo imaging was performed with white rabbits weighing approximately 3.5 kg. The rabbits were anesthetized with I mL/kg Rabbit Mix (8:5:2 ratio of xylazine hydrochloride, 20 mg/mL; ketamine hydrochloride, 10 mg/mL; and acepromazine maleate, 100 mg/mL) administered intramuscularly.

Intravenous injections of saline or air-filled polymeric microcapsules were performed through the marginal ear vein using a 23-gauge butterfly catheter. Ultrasound imaging was performed with the Acuson scanner using a 7.5-MHz high-resolution linear transducer. Imaging of the aorta was performed before and after administering the contrast agent. Both B-mode and Doppler images were established.

The color Doppler ultrasound is a particularly sensitive detector of bubbles. The effect of an ultrasonic contrast agent is readily identifiable by a sudden marked increase in the amplitude of the audible Doppler signal and easily recognized by all listeners. There is also a change in the quality of the Doppler sound, consisting primarily of an apparent increase in pitch.

To verify that the air bubbles remained encapsulated in the microcapsule during in vivo application, a B-mode sector image of an aorta was taken after first injecting 5 mL saline, and then injecting 1 mL and then 2 mL of solutions containing PCPP polymeric microcapsules ($1\times10^6$ particles/mL) with a period of 5 minutes between each injection. No echoes were reflected from the aorta after the saline injection. However, immediately after injecting polymeric microcapsules, the aorta was filled with echogenic microcapsules. Injecting an additional 2 mL of microcapsules resulted in a very strong echo, giving a clear image of the blood vessel and demonstrating that these microcapsules were highly echogenic. The echo from the aorta lasted for more than 15 minutes, and it seemed that its intensity did not decline with time.

A color Doppler image of the aorta approximately 15 minutes after injection showed a significant increase in the image and the signal. Pictures were taken 15 and 20 minutes after injection, demonstrating that the PCPP microcapsules are very stable in vivo (can survive the high pressure of the left chambers of the heart), can pass the capillary bed of the lung and are very echogenic.

Variations and modifications of the compositions, methods of preparing the compositions, and methods of using the compositions will be obvious to those with ordinary skill in the art. It is intended that all of these variations and modifications be included within the scope of the appended claims.

We claim:

1. A microcapsule having a diameter of 700 microns or less formed of biocompatible hydrogel formed by crosslinking with a multivalent ion of a polymer selected from the group consisting of poly(phosphazenes), poly(acrylic acids), poly(methacrylic acids), copolymers of acrylic acid or methacrylic acid and polyvinyl ethers or poly(vinyl acetate), and sulfonated polystyrene, comprising a gas encapsulated therein in an amount effective for use as an imaging agent.

2. The microcapsule of claim 1 wherein the diameter of the microcapsule is between one and ten microns.

3. The microcapsule of claim 1 wherein the hydrogel is prepared from an ionically crosslinkable synthetic polymer that is partially soluble in a gasified aqueous solution prior to crosslinking and has charged side groups which are crosslinked by reacting the side groups with multivalent ions of the opposite charge.

4. The microcapsule of claim 3 wherein the side groups are acidic and the ions are cations.

5. The microcapsule of claim 4 wherein the polymer is a polyelectrolyte selected from the group consisting of poly(phosphazenes), poly(acrylic acids), poly(methacrylic acids), copolymers of acrylic acid or methacrylic acid and polyvinyl ethers or poly(vinyl acetate), sulfonated polystyrene, and the polymer is soluble in an aqueous solution selected from the group consisting of water, aqueous alcohol, and buffered aqueous salt solutions.

6. The microcapsules of claim 4 wherein the acidic side groups contain moieties selected from the group consisting of carboxylic acid, sulfonic acid, halogenated alcohol, phenolic OH, and acidic OH groups.

7. The microcapsules of claim 4 wherein the multivalent cation is selected from the group consisting of calcium, copper, aluminum, magnesium, strontium, barium, tin, zinc and organic cations.

8. The microcapsule of claim 3 wherein the side groups are basic and the ions are anions.

9. The microcapsules of claim 8 wherein the anions are selected from group consisting of dicarboxylic acids, sulfate ions and carbonate ions.

10. The microcapsules of claim 3 wherein the charged groups on the surface are further complexed with a multivalent polyion of the opposite charge to form a semi-permeable membrane.

11. The microcapsules of claim 10 wherein the hydrogel is liquefied within the semi-permeable membrane by removing the multivalent ions.

12. A method for preparing synthetic polymeric crosslinked microcapsules encapsulating imaging contrast agents comprising the steps of:

a) entrapping gas bubbles in an aqueous solution or dispersion of an ionically crosslinkable synthetic polymer selected from the group consisting of poly(phosphazenes), poly(acrylic acids), poly(methacrylic acids), copolymers of acrylic acid or methacrylic acid and polyvinyl ethers or poly(vinyl acetate), and sulfonated polystyrene, that has charged side groups, and b) reacting the polymer with a multivalent ion of the opposite charge to form an ionically crosslinked hydrogel microparticle having a maximum diameter of 700 microns or less encapsulating an amount of gas effective for use as an imaging agent.

13. The method of claim 12 wherein the gas is entrapped in the polymer solution or dispersion by sonication of the polymer in the presence of the gas.

14. The method of claim 12 wherein the gas is mixed with the polymer solution or dispersion and atomized through an orifice forming droplets which are dispersed into the crosslinking solution.

15. The method of claim 12 wherein the polymer is a polyelectrolyte selected from the group consisting of polyphosphazenes, polyacrylic acids, polymethacrylic acids, copolymers of acrylic acid and polyvinyl acetate, polyvinyl ethers, polysulfonic acid derivatives, and polystyrene sulfonates and is soluble in an aqueous solution selected from the group.

16. The method of claim 15 wherein the multivalent ion is selected from the group consisting of calcium, copper, aluminum, magnesium, strontium, barium, tin, zinc and organic cations.

17. The method of claim 12 wherein the charged side groups are further complexed with a multivalent polyion of the opposite charge to form a semi-permeable membrane; and wherein the method further comprises liquefying the gel after forming the semi-permeable membrane to form a microcapsule.

18. A method for ultrasonic imaging for use in medical procedures, comprising the steps of:

a) administering microcapsules having a diameter of 700 microns or less formed of an ionically crosslinked biocompatible hydrogel formed from a polymer selected from the group consisting of poly(phosphazenes), poly(acrylic acids), poly(methacrylic acids), copolymers of acrylic acid or methacrylic acid and polyvinyl ethers or poly(vinyl acetate), and sulfonated polystyrene, having a gas encapsulated therein in an amount effective for use as an imaging agent into a mammal to alter the acoustic properties of a predetermined area; and b) ultrasonically scanning a predetermined area to obtain an image of the area.

19. The method of claim 19 wherein the diameter of the microcapsule is between one and ten microns.

20. The method of claim 18 wherein the hydrogel is prepared from an ionically crosslinkable synthetic polymer that is partially soluble in a gasified aqueous solution prior to crosslinking and has charged side groups which are crosslinked by reacting the side groups with multivalent ions of the opposite charge.

* * * * *

UNITED STATES PATENT AND TRADEMARK OFFICE
CERTIFICATE OF CORRECTION

PATENT NO. : 5,487,390
DATED : January 30, 1996
INVENTOR(S) : Smadar Cohen, Alexander K. Andrianov, Margaret Wheatley, Harry R. Allcock and Robert S. Langer It is certified that error appears in the above-identified patent and that said Letters Patent is hereby corrected as shown below:

Claim 15, column 20, line 4, insert between "group" and the period
--consisting of water, aqueous alcohol, and buffered aqueous salt solutions--

Signed and Sealed this

Thirteenth Day of June, 2000

Attest:

Q. TODD DICKINSON

*Attesting Officer*      *Director of Patents and Trademarks*